US012690806B2

(12) United States Patent
Chen et al.

(10) Patent No.: US 12,690,806 B2
(45) Date of Patent: Jul. 28, 2026

(54) SLEEP MONITORING SYSTEM AND SLEEP MONITORING METHOD

(71) Applicant: WISTRON NEWEB CORPORATION, Hsinchu (TW)

(72) Inventors: Yi-An Chen, Hsinchu (TW); Chui-Chu Cheng, Hsinchu (TW); Tsung-Yu Ho, Hsinchu (TW)

(73) Assignee: WISTRON NEWEB CORPORATION, Hsinchu (TW)

( * ) Notice: Subject to any disclaimer, the term of this patent is extended or adjusted under 35 U.S.C. 154(b) by 359 days.

(21) Appl. No.: 18/517,154

(22) Filed: Nov. 22, 2023

(65) Prior Publication Data

US 2024/0180483 A1     Jun. 6, 2024

(30) Foreign Application Priority Data

Dec. 1, 2022    (TW) ................................. 111146088

(51) Int. Cl.
*A61B 5/00*          (2006.01)
*A61B 5/08*          (2006.01)

(52) U.S. Cl.
CPC .......... *A61B 5/4815* (2013.01); *A61B 5/0022* (2013.01); *A61B 5/0816* (2013.01); *A61B 5/4812* (2013.01); *A61B 5/7203* (2013.01); *A61B 5/7257* (2013.01)

(58) Field of Classification Search
CPC ... A61B 5/4815; A61B 5/0022; A61B 5/0816; A61B 5/4812; A61B 5/7203; A61B 5/7257; A61B 5/00
See application file for complete search history.

(56) References Cited

U.S. PATENT DOCUMENTS

| | | | | |
|---|---|---|---|---|
| 11,439,344 | B2 * | 9/2022 | Zhang | .................... G16H 40/67 |
| 2020/0397365 | A1 * | 12/2020 | Zhang | .................... G16H 50/20 |
| 2022/0104704 | A1 * | 4/2022 | Zakharov | ............. A61B 5/4815 |

FOREIGN PATENT DOCUMENTS

| | | | | | |
|---|---|---|---|---|---|
| CN | 108778106 | A | | 11/2018 | |
| CN | 109363647 | A | | 2/2019 | |
| CN | 114680840 | A | * | 7/2022 | ........... A61B 5/7253 |
| CN | 114916912 | A | * | 8/2022 | ........... A61B 5/4818 |
| CN | 115120206 | A | * | 9/2022 | ........... A61B 5/7203 |
| CN | 116348029 | A | * | 6/2023 | ........... A61B 5/4809 |
| WO | WO-2017156492 | A1 | * | 9/2017 | ............. G01S 13/88 |
| WO | WO-2021158137 | A1 | * | 8/2021 | ........... A61B 5/4812 |
| WO | WO-2022031038 | A1 | * | 2/2022 | ........... A61B 5/6889 |
| WO | WO-2022073112 | A1 | * | 4/2022 | ............. A61B 5/743 |

\* cited by examiner

*Primary Examiner* — Navin Natnithithadha
(74) *Attorney, Agent, or Firm* — McClure, Qualey & Rodack, LLP

(57)          ABSTRACT

A sleep monitoring system and a sleep monitoring method are provided. The sleep monitoring system includes a receiver, a transmitter, a storage and a processing circuit. The receiver and the transmitter are disposed in the target field, and the transmitter transmits a wireless detection signal to the target field. The user is located between the receiver and the transmitter, and the receiver receives the wireless detection signal over multiple communication links. The processing circuit is electrically connected to the receiver and the storage, and analyzes a change of the wireless detection signal within a predetermined time, so as to detect a sleep time of a user within the predetermined time, and obtains a sleep quality of the user within the sleep time.

18 Claims, 11 Drawing Sheets

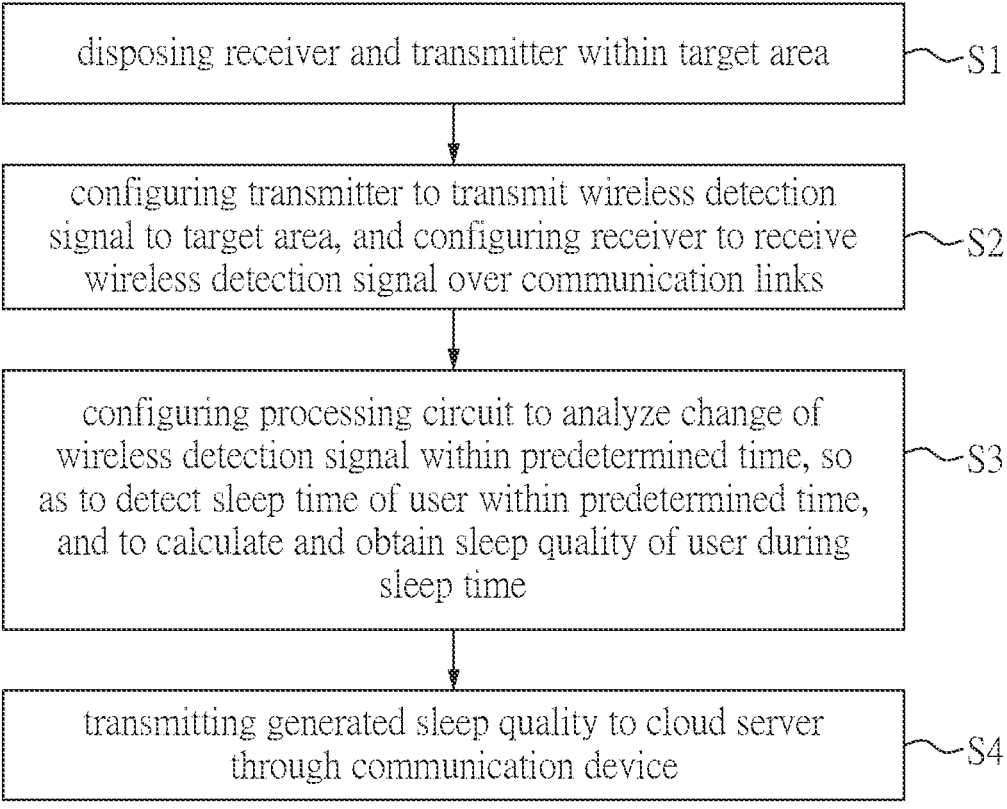

disposing receiver and transmitter within target area ~~S1 configuring transmitter to transmit wireless detection signal to target area, and configuring receiver to receive wireless detection signal over communication links ~~S2 configuring processing circuit to analyze change of wireless detection signal within predetermined time, so as to detect sleep time of user within predetermined time, and to calculate and obtain sleep quality of user during sleep time ~~S3 transmitting generated sleep quality to cloud server through communication device ~~S4

FIG. 3

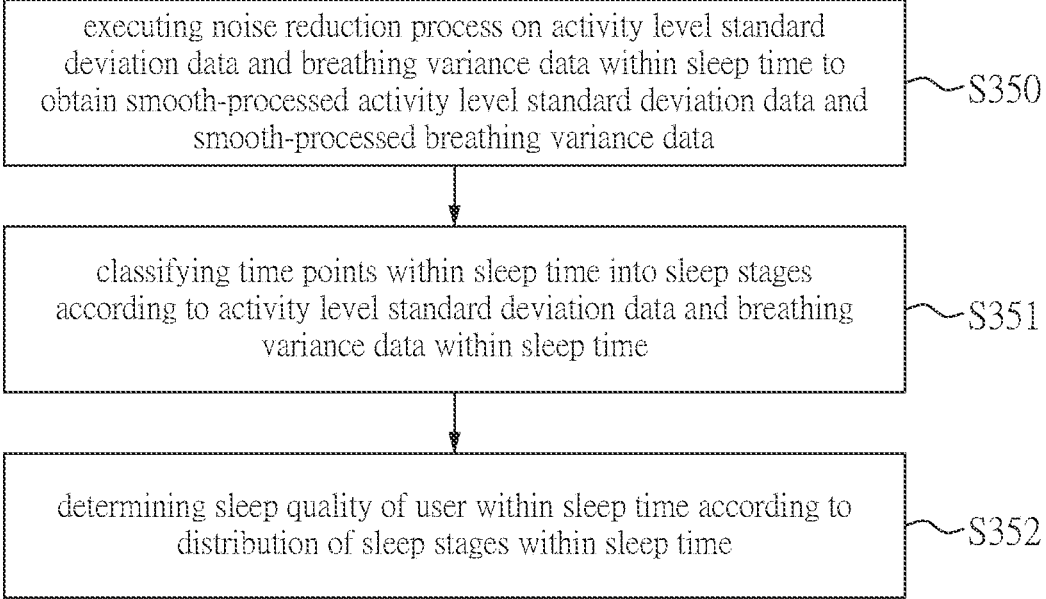

executing noise reduction process on activity level standard deviation data and breathing variance data within sleep time to obtain smooth-processed activity level standard deviation data and smooth-processed breathing variance data ~S350 classifying time points within sleep time into sleep stages according to activity level standard deviation data and breathing variance data within sleep time ~S351 determining sleep quality of user within sleep time according to distribution of sleep stages within sleep time ~S352

FIG. 9

SLEEP MONITORING SYSTEM AND SLEEP MONITORING METHOD

CROSS-REFERENCE TO RELATED PATENT APPLICATION

This application claims the benefit of priority to Taiwan Patent Application No. 111146088, filed on Dec. 1, 2022. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a monitoring system and a monitoring method, and more particularly to a sleep monitoring system and a sleep monitoring method.

BACKGROUND OF THE DISCLOSURE

Studies have shown that certain health problems are closely related to sleep quality. Health problems such as apnea and high blood pressure, among others, can be detected early by observing the sleep quality.

In recent years, there are many wearable products on the market that monitor sleep quality, such as health bracelets and smart watches, which can detect the user's movements and heart rhythm. However, users must wear such a watch or bracelet overnight, which may cause discomfort during sleep and itself affect sleep quality. In addition, since the battery power of the wearable device is limited, sleep quality of a user cannot be monitored while the wearable device is charging.

Therefore, in order to achieve early detection of potential health problems, development of a non-contact sleep monitoring technology that can help users observe their own long-term sleep quality has become one of the important issues in the related art.

SUMMARY OF THE DISCLOSURE

In response to the above-referenced technical inadequacies, the present disclosure provides a sleep monitoring system and a sleep monitoring method capable of realizing the non-contact sleep monitoring technology based on wireless signals and completing an analysis of sleep quality in wireless terminal equipment, thereby allowing users to acquire more information about their sleep time and sleep quality.

In one aspect, the present disclosure provides a sleep monitoring system, which includes a receiver, a transmitter, a storage unit and a processing circuit. The receiver is disposed in a target field. The transmitter is disposed in the target field, and is configured to transmit a wireless detection signal to the target field. A user is located between the receiver and the transmitter, and the receiver is configured to receive the wireless detection signal through a plurality of communication links. The processing circuit is electrically connected to the receiver and the storage unit, and the processing circuit is configured to analyze a change of the wireless detection signal within a predetermined time, so as to detect a sleep time of the user within the predetermined time, and to calculate and obtain a sleep quality of the user during the sleep time.

In another aspect, the present disclosure provides a sleep monitoring method, which includes: disposing a receiver and a transmitter within a target area, wherein a user is located between the receiver and the transmitter; configuring the transmitter to transmit a wireless detection signal to the target area, and configuring the receiver to receive the wireless detection signal over a plurality of communication links; and configuring a processing circuit electrically connected to the receiver and the storage unit to analyze a change of the wireless detection signal within a predetermined time, so as to detect a sleep time of the user within the predetermined time, and to calculate and obtain a sleep quality of the user during the sleep time.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which:

FIG. 3 is a flowchart of a sleep monitoring method according to one embodiment of the present disclosure;

FIG. 9 is a detailed flowchart of step S35 in FIG. 4;

DETAILED DESCRIPTION OF THE EXEMPLARY EMBODIMENTS

Figure 1:
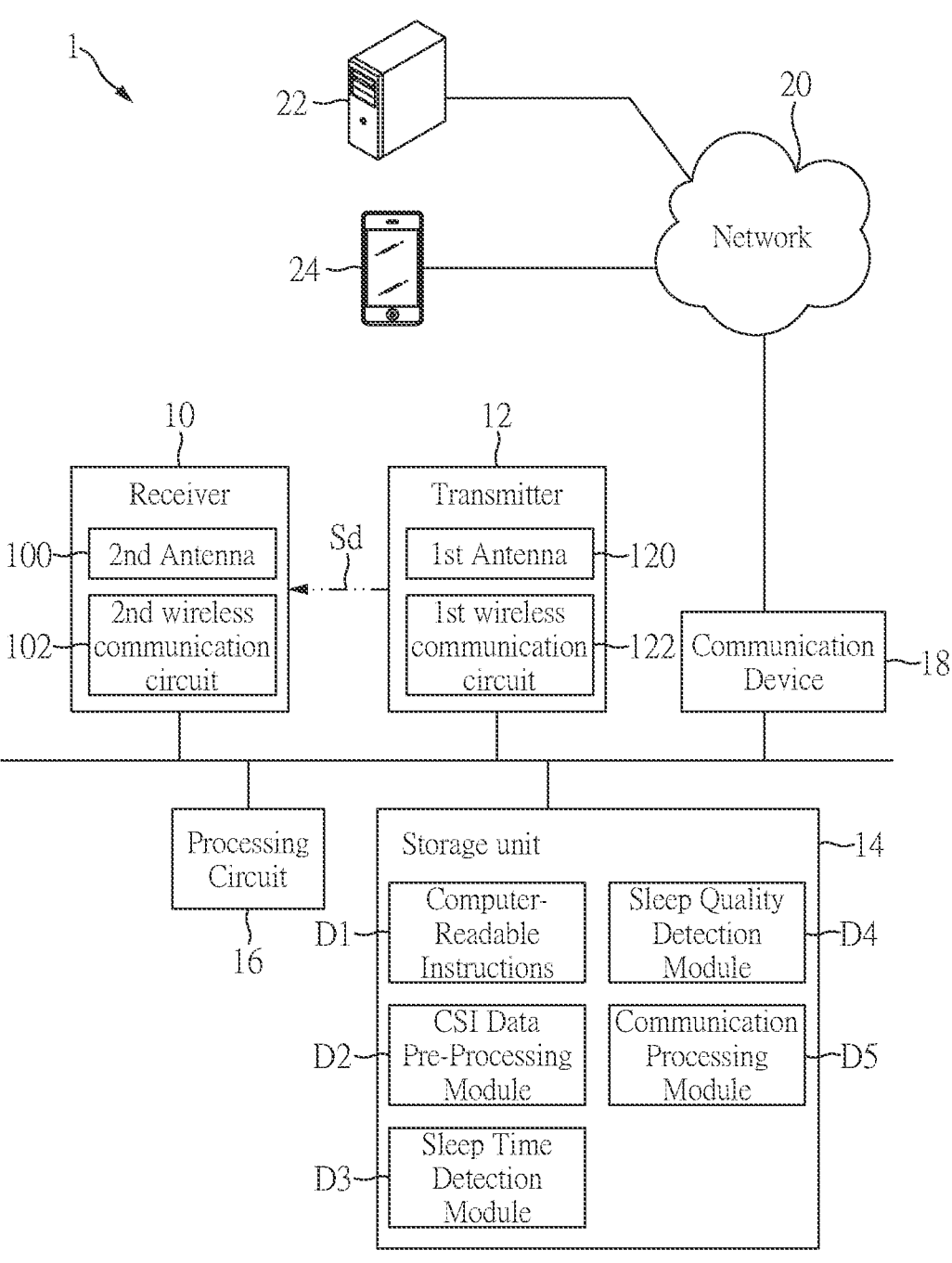
FIG. 1 is a functional block diagram of a sleep monitoring system according to one embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a," "an" and "the" includes plural reference, and the meaning of "in" includes "in" and "on." Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first," "second" or "third" can be used to describe various components, signals or the like, which are for distinguishing one component/signal from another one only, and are not intended to, nor should be construed to impose any substantive limitations on the components, signals or the like.

Figure 2:
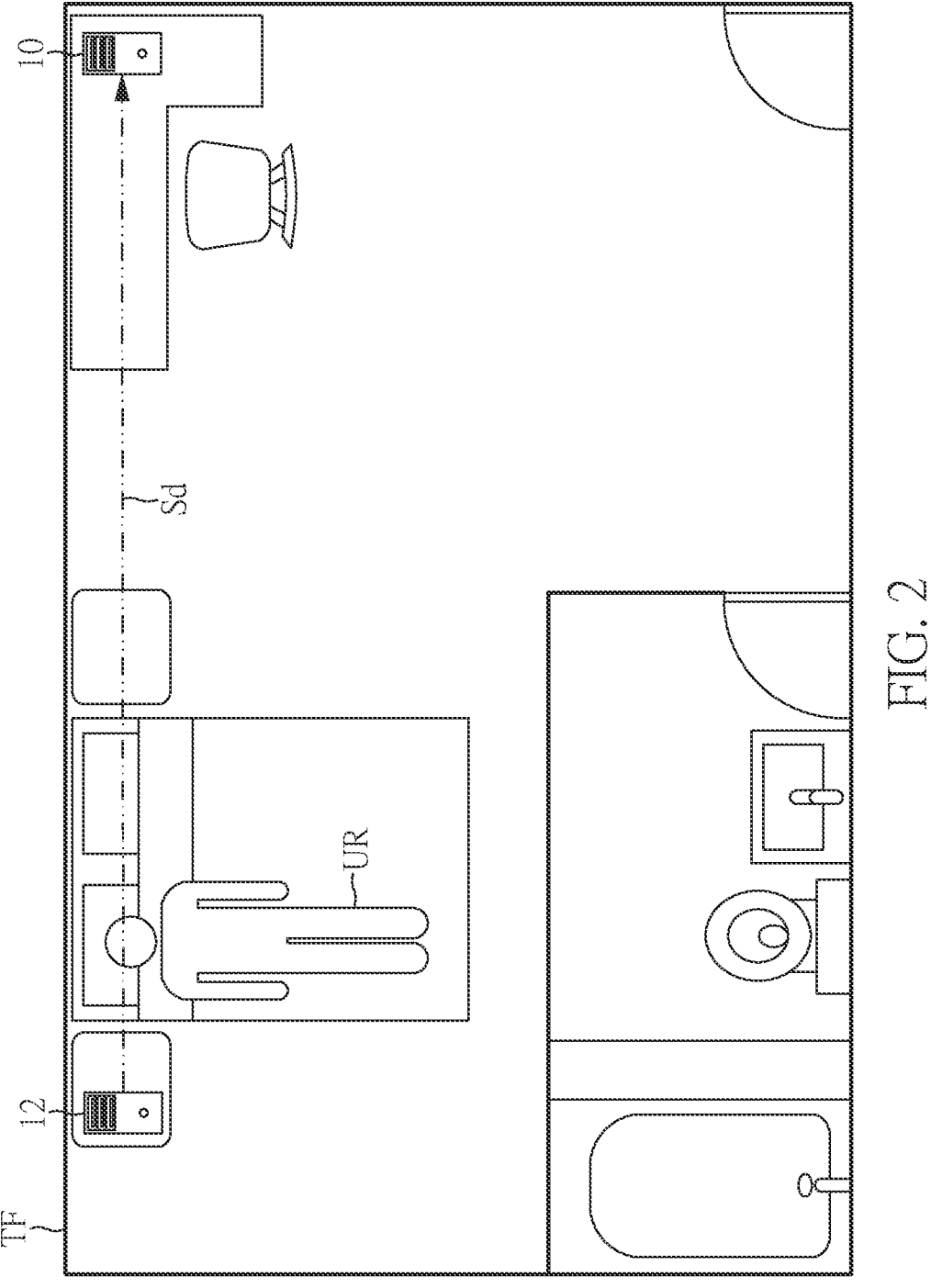
FIG. 2 is a schematic diagram of the sleep monitoring system configured in a target field for sleep monitoring according to one embodiment of the present disclosure.

FIG. 1 is a functional block diagram of a sleep monitoring system according to one embodiment of the present disclosure. FIG. 2 is a schematic diagram of the sleep monitoring system configured in a target field for sleep monitoring according to one embodiment of the present disclosure.

Referring to FIG. 1 and FIG. 2, one embodiment of the present disclosure provides a sleep monitoring system 1, which includes a receiver 10, a transmitter 12, a storage unit 14, a processing circuit 16 and a communication device 18. As shown in FIG. 2, the receiver 10 and the transmitter 12 can be installed in a target field TF, such as indoor spaces like a residence or a bedroom, and a sleep monitoring range can be set, such that a position where a user UR is scheduled to sleep is located between the receiver 10 and the transmitter 12.

The transmitter 12 can include a first antenna 120 and a first wireless communication circuit 122 for controlling a transmission direction of the first antenna 120. The transmitter 12 is configured to transmit a wireless detection signal Sd to the target field TF, for example, the wireless detection signal Sd can be transmitted to the aforementioned sleep monitoring range. The first wireless communication circuit 122 can support multiple protocols, and can be used to transmit wireless detection signals Sd with different operating frequencies. In addition, the above-mentioned protocols can include, for example, a wireless communication standard, such as IEEE 802.11, 3G/4G/5G standard.

Similarly, the receiver 10 can include a second antenna 100 and a second wireless communication circuit 102 for controlling a transmission direction of the second antenna 100. Similarly, the second wireless communication circuit 102 can support multiple protocols corresponding to the transmitter 12, and can be used to transmit the wireless detection signal Sd with different operating frequencies. In addition, the protocols can include wireless communication standards, such as IEEE 802.11, 3G/4G/5G standards, and the receiver 10 can be configured to receive the wireless detection signal Sd over multiple communication links. In one embodiment, the receiver 10 and the transmitter 12 can communicate with each other through the network.

The storage unit 14 can be, for example, but not limited to, a hard disk, a solid-state disk, or other storage devices that can store data, and the storage unit 14 is configured to store at least a plurality of computer-readable instructions D1, a CSI data pre-processing module D2, a sleep time detection module D3, a sleep quality detection module D4 and a communication processing module D5.

The processing circuit 16 is electrically connected to the receiver 10 and the storage unit 14. The processing circuit 16 can include one or more processors, and can be, for example, a combination of any of a central processing unit (CPU) and/or a general-purpose microprocessor, a microcontroller, a digital signal processor (DSP), a field programmable gate array (FPGA), a programmable logic device (PLD), a controller or any other suitable circuits, devices and/or structures capable of performing data calculations or other operations. In one embodiment of the present disclosure, the processing circuit 16 can be configured to analyze a change of the wireless detection signal Sd within a predetermined time, so as to detect the sleep time of the user within the predetermined time, and calculate and obtain a sleep quality of the user during the sleep time.

The communication device 18 is electrically connected to the processing circuit 16. The communication device 18 can be, for example, a network interface card or a router, which is configured to access the network 20 under control of the processing circuit 16. The communication device 18 can be connected to a cloud server 22 through the network 20, and the sleep quality generated by the processing circuit 16 can be transmitted to the cloud server 22. In addition, the user device 24 can be a mobile electronic device, such as a smart phone, a notebook computer, a tablet computer or the like. The user device 24 can communicate with the cloud server 22 and each device and component in the sleep monitoring system 1 through the network 20, and can be used to display the sleep quality generated by the processing circuit 16 with a built-in user interface provided in the user device 24.

In this embodiment, the sleep monitoring system 1 provided by the present disclosure can operate based on a WI-FI network in the target field TF, for example, and the sleep monitoring system 1 can be deployed through WI-FI mesh network devices. In addition, since the WI-FI network has an advantage of being low in cost, the sleep monitoring system 1 provided by the present disclosure is easy to deploy, manage, and maintain.

FIG. 3 is a flowchart of a sleep monitoring method according to one embodiment of the present disclosure. Reference is made to FIG. 3, one embodiment of the present disclosure provides a sleep monitoring method, which at least includes the following steps:

Step S1: disposing the receiver and the transmitter within the target area.

Step S2: configuring the transmitter to transmit the wireless detection signal to the target area, and configuring the receiver to receive the wireless detection signal over the communication links.

Step S3: configuring the processing circuit to analyze the change of the wireless detection signal within the predetermined time, so as to detect a sleep time of the user within the predetermined time, and to calculate and obtain a sleep quality of the user during the sleep time. As shown in FIG. 2, the transmitter 12 and the receiver 10 can be arranged in the bedroom, and then the processing circuit 16 will continuously capture the wireless detection signal Sd between the transmitter 12 and the receiver 10. Taking the WI-FI signals as an example, the WI-FI signals vary to different extents while being transmitted through the user UR. The sleep monitoring system 100 then detects the user's sleep time and calculates the sleep quality by analyzing the change of the WI-FI signals.

Figure 4:
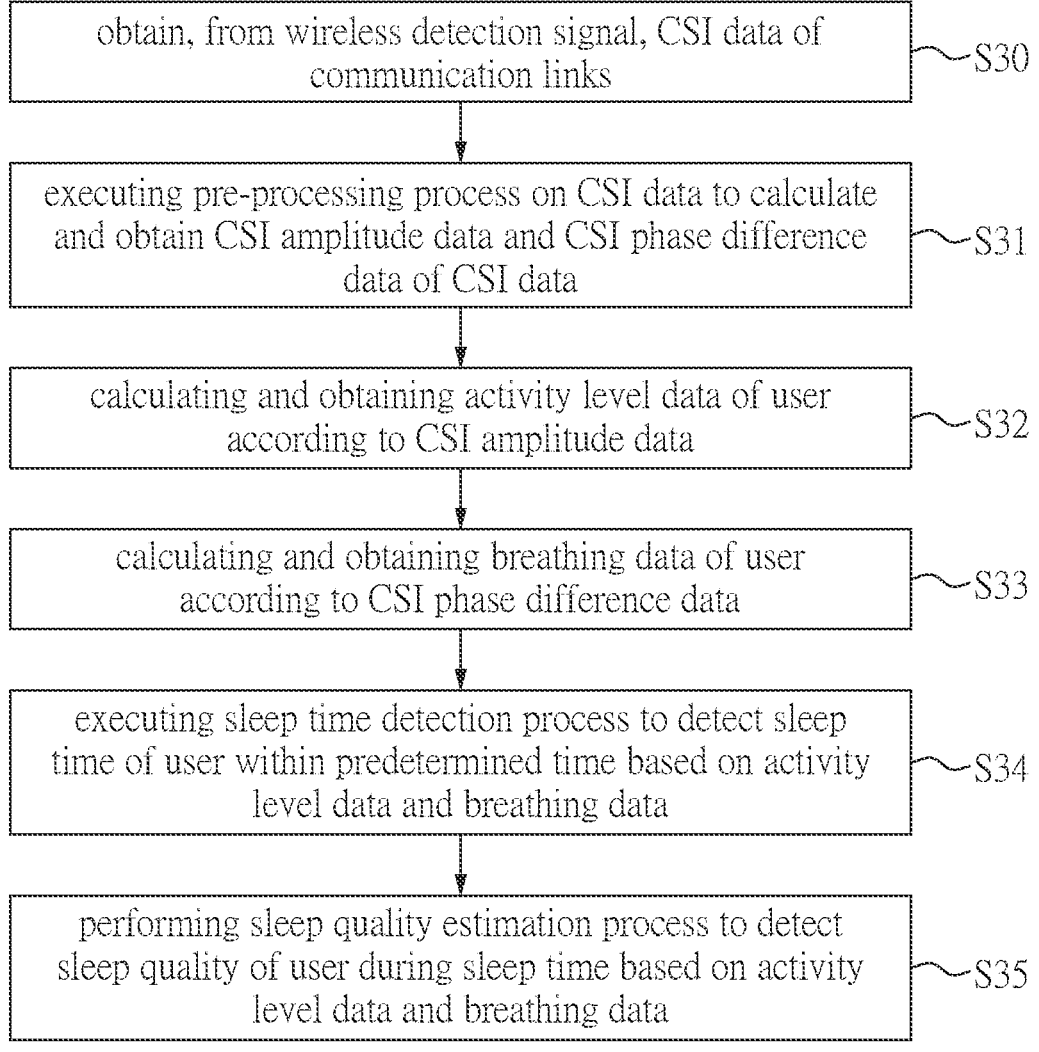
FIG. 4 is a detailed flowchart of step S3 in FIG. 3.

FIG. 4 is a detailed flowchart of step S3 in FIG. 3. Reference is made to FIG. 4. Step S3 further includes the following steps:

Step S30: obtain, from the wireless detection signal, channel state information (CSI) data of the communication links.

In detail, the CSI data describes how a wireless signal propagates from the transmitter 12 to the receiver 10 at a specific carrier frequency. The CSI data includes amplitude and phase, which are affected by multipath changes caused by human motion and breathing frequency. In the embodiment of the present disclosure, the CSI data obtained based on the WI-FI wireless signal can realize a non-contact sleep monitoring, and has advantages of wide coverage, easy deployment and low cost.

Figure 5:
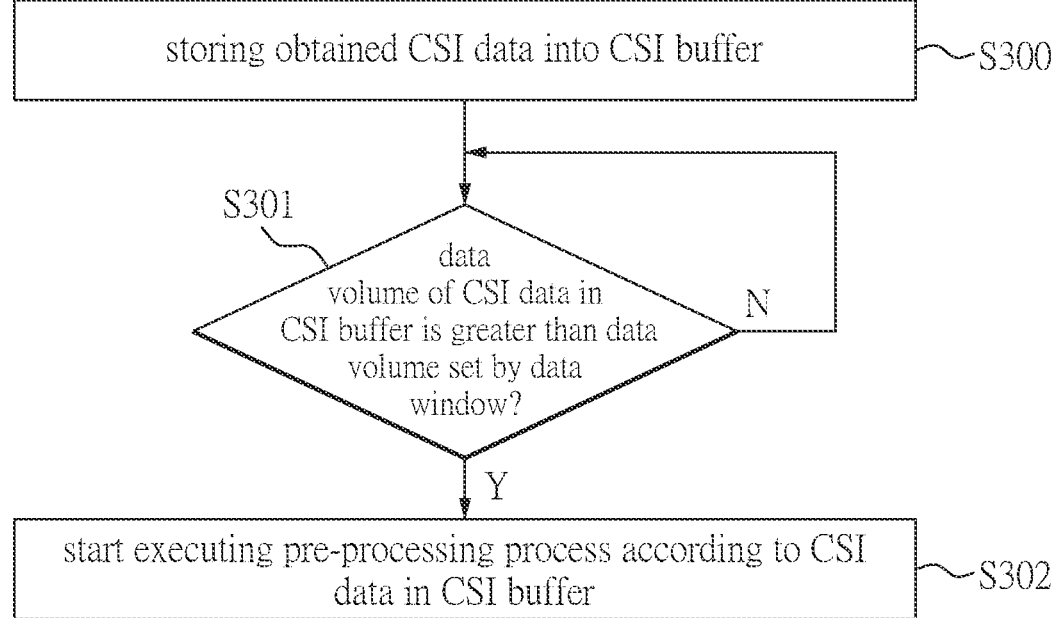
FIG. 5 is another flowchart of the sleep monitoring method according to one embodiment of the present disclosure.

Reference is made to FIG. 5, which is another flowchart of the sleep monitoring method according to one embodiment of the present disclosure. It should be noted that once a data volume of the CSI data is accumulated to a certain extent, the obtained CSI data is sufficient to evaluate the sleep time and sleep quality. Therefore, in the sleep monitoring method in FIG. 4, the processing circuit is also configured to perform the following steps:

Step S300: storing the obtained CSI data into a CSI buffer.

Step S301: determine whether or not a data volume of the CSI data in the CSI buffer is greater than a data volume set by a data window. The data volume referred to in this step can be a length of time for collecting the CSI data, for example, several seconds or minutes, or can refer to a data size of the CSI data.

If so, the method proceeds to step S302: start executing the pre-processing process according to the CSI data in the CSI buffer.

If not, the method repeats step S301 until the data volume of the CSI data in the buffer is greater than the data volume set by the data window.

Referring to FIG. 4 again, the method proceeds to step S31: executing a pre-processing process on the CSI data to calculate and obtain CSI amplitude data and CSI phase difference data of the CSI data.

Figure 6:
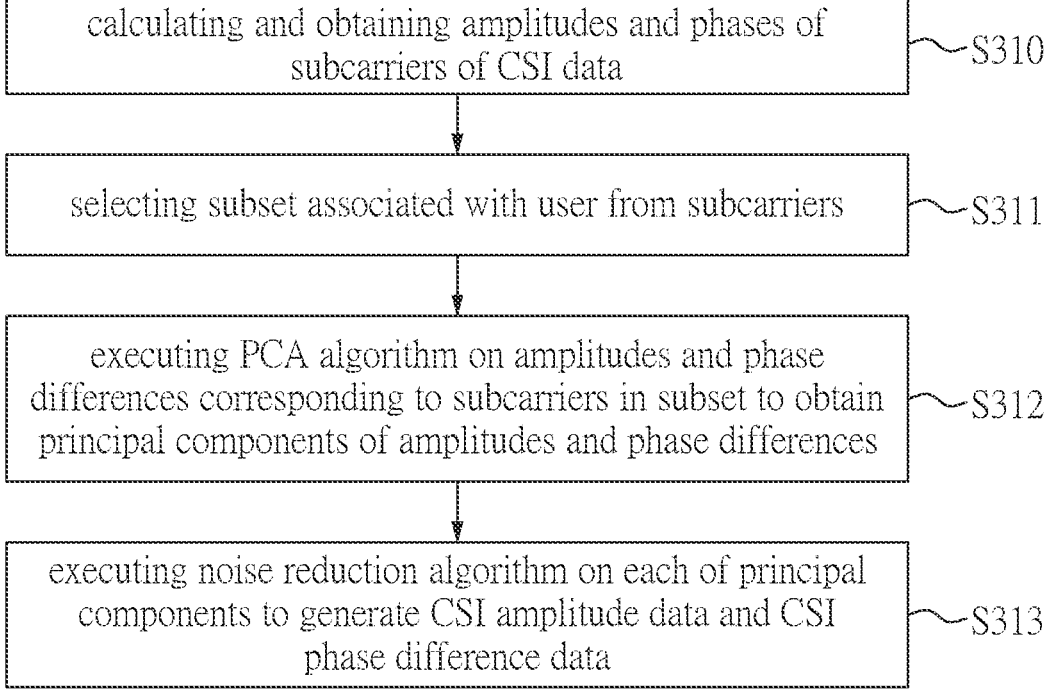
FIG. 6 is a detailed flowchart of step S31 in FIG. 4.

Details associated with this step can further be referenced in FIG. 6, which is a detailed flowchart of step S31 in FIG. 4. As shown in FIG. 6, the processing circuit 16 can execute the CSI data pre-processing module D2 to execute the pre-processing process of step S31, which can include the following steps:

Step S310: calculating and obtaining a plurality of amplitudes and a plurality of phases of a plurality of subcarriers of the CSI data.

As mentioned earlier, the CSI data includes amplitudes and phases. More specifically, the CSI data is composed of the amplitudes and phases of a plurality of subcarriers. When multiple subcarriers arrive at the receiver 10 along the multipath channel, each of the subcarriers has a specific amplitude and phase. Therefore, the processing circuit 16 can process the CSI data to obtain the amplitude and the phase of the subcarrier.

Step S311: selecting a subset associated with the user from the plurality of subcarriers. For example, the CSI data includes the subcarriers over the multipath links in space; however, not every one of the subcarriers can reflect the user's activity level. Therefore, in this step, the amplitude of each subcarrier in the CSI data will be counted, and amplitude changes will be ranked. Top few subcarriers with large amplitude changes and non-noise are then selected from the CSI data as a subset related to the user. In the meanwhile, the phase of each subcarrier in the CSI data is also counted to obtain the subcarriers corresponding to large frequency changes and non-noises, which are regarded as the subset related to the user. Then, a breathing rate and activity level of the user can be detected for each subcarrier in the subset. It should be noted that the subsets selected for the breathing rate and activity level can be the same, or can be selected separately.

Step S312: executing a principal component analysis (PCA) algorithm on the amplitudes and phase differences corresponding to the plurality of subcarriers in the subset to obtain principal components of the plurality of amplitudes and the plurality of phase differences. In short, the PCA algorithm can be executed to reduce dimensionality of a data set corresponding to the subset, while retaining features that contribute the most to a variance in the data set. For example, orthogonal transformation can be used to linearly transform observed values of a series of possibly related variables, so as to be projected into values of a series of linearly uncorrelated variables. These uncorrelated variables are called principal components. In this way, amount of calculation required for sleep monitoring can be effectively reduced, and it can also be ensured that calculation results in the sleep monitoring can effectively reflect characteristics of the data set.

Step S313: executing a noise reduction algorithm on each of the principal components to generate the CSI amplitude data and the CSI phase difference data. This step is to reduce noise in data such as the amplitudes and the phase differences corresponding to the principal components.

Referring to FIG. 4 again, the sleep monitoring method proceeds to step S32: calculating and obtaining activity level data of the user according to the CSI amplitude data. For example, when the sleep monitoring system 1 is deployed in the target field TF, the CSI data of the target field TF can be firstly collected under a non-interference environment (for example, no one is in the target field TF), then CSI data of the target field TF is collected when the user enters the target field TF, and the aforementioned pre-processing process is then performed. After subtracting amplitude data in the pre-processed CSI data, amplitude data that can reflect the activity level of the user can be obtained, and a corresponding activity level can be generated according to variations of the amplitudes in the subtracted amplitude data. For example, the variations in the amplitudes can be normalized, with higher amplitude changes corresponding to higher activity level values and lower amplitude changes corresponding to lower activity level values.

Step S33: calculating and obtaining breathing data of the user according to the CSI phase difference data. For example, a Fourier transform algorithm, such as Fast Fourier transform (FFT), can be performed on the CSI phase difference data to convert the CSI phase difference data from time domain to frequency domain. A main frequency that determines the overall CSI phase difference data and corresponds to the user's breathing rate can be determined according to the CSI phase difference data, such that multiple records of breathing rate data can be obtained as the breathing data.

Step S34: executing a sleep time detection process to detect the sleep time of the user within the predetermined time based on the activity level data and the breathing data.

Figure 7:
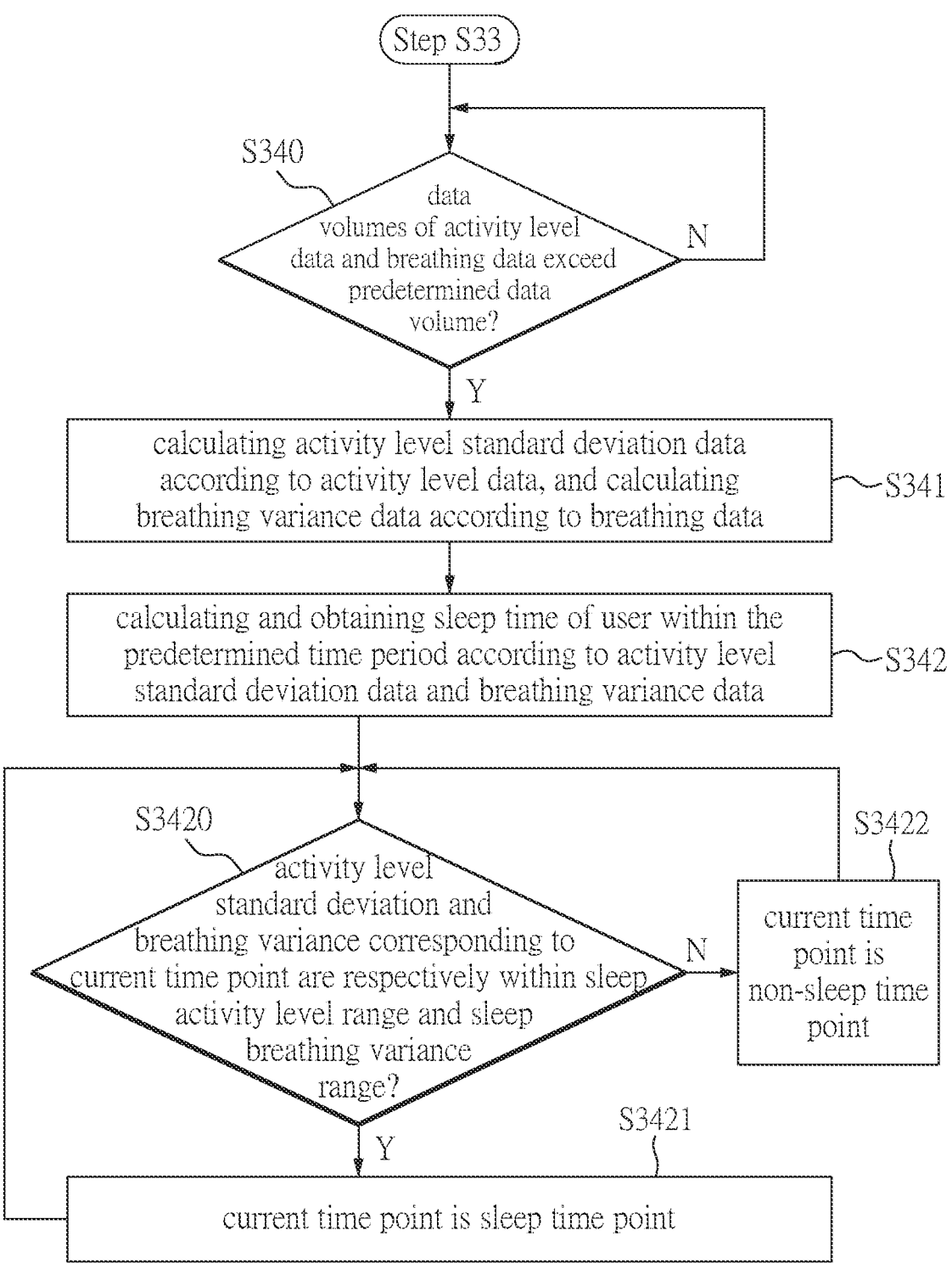
FIG. 7 is a detailed flowchart of step S34 in FIG. 4.

Reference is made to FIG. 7, which is a detailed flowchart of step S34 in FIG. 4. In the sleep monitoring method provided by the present disclosure, the processing circuit 16 can execute the sleep time detection module D3 to execute the sleep time detection process in step S34, which may include the following steps:

Step S340: determining whether or not data volumes of the activity level data and the breathing data exceed a predetermined data volume. In detail, this step requires a sufficient amount of data to accurately determine the sleep time. Therefore, the so-called predetermined data volume can be the length of time for collecting the activity level data and the breathing data, for example, several minutes or hours, or it can refer to a data size of the activity level data and the breathing data.

If so, the sleep time detection process proceeds to step S341; if not, the sleep time detection process repeats step S34 until the data volume of the activity level data and the breathing data exceed the predetermined data volume.

Step S341: calculating an activity level standard deviation data according to the activity level data, and calculating a breathing variance data according to the breathing data. For example, the activity level at different time points within the predetermined time (for example, if the predetermined time is 1 hour, and an interval between the time points is 1 minute, then there are 60 time points) can be calculated to obtain a plurality of activity level standard deviations corresponding to the time points to serve as the activity level standard deviation data. The breathing rates at different time points within the predetermined time can also be counted to obtain variances of the breathing rates corresponding to the different time points to serve as the breathing variance data.

Step S342: calculating and obtaining the sleep time of the user within the predetermined time period according to the activity level standard deviation data and the breathing variance data. For example, when a person is asleep, their breathing rate decreases and their activity level also decreases. Therefore, the user's daily activity amount can be counted, and accordingly, the sleep activity level range and the sleep breathing variance range of the same user in a sleep state can be set to enable determination of whether or not the user has fallen asleep. In more detail, step S342 can include performing the following steps for each time point within the predetermined time:

Step S3420: determining whether or not the activity level standard deviation and the breathing variance corresponding to a current time point are respectively within a sleep activity level range and a sleep breathing variance range.

If so, the method proceeds to step S3421: determining that the current time point is a sleep time point. The method then returns to step S3420 to determine the next time point. If not, the method proceeds to step S3422: determining that the current time point is a non-sleep time point. The method then returns to step S3420 to determine the next time point. After all the time points within the predetermined time have been determined, an accurate sleep time can be obtained from the predetermined time. In this step, statistical values are obtained after a period of time by recording the breathing rate and the activity level, and the statistical values of the breathing rate and the activity level are assessed at the same time, such that the determination of the sleep state can be more accurate.

Figure 8:
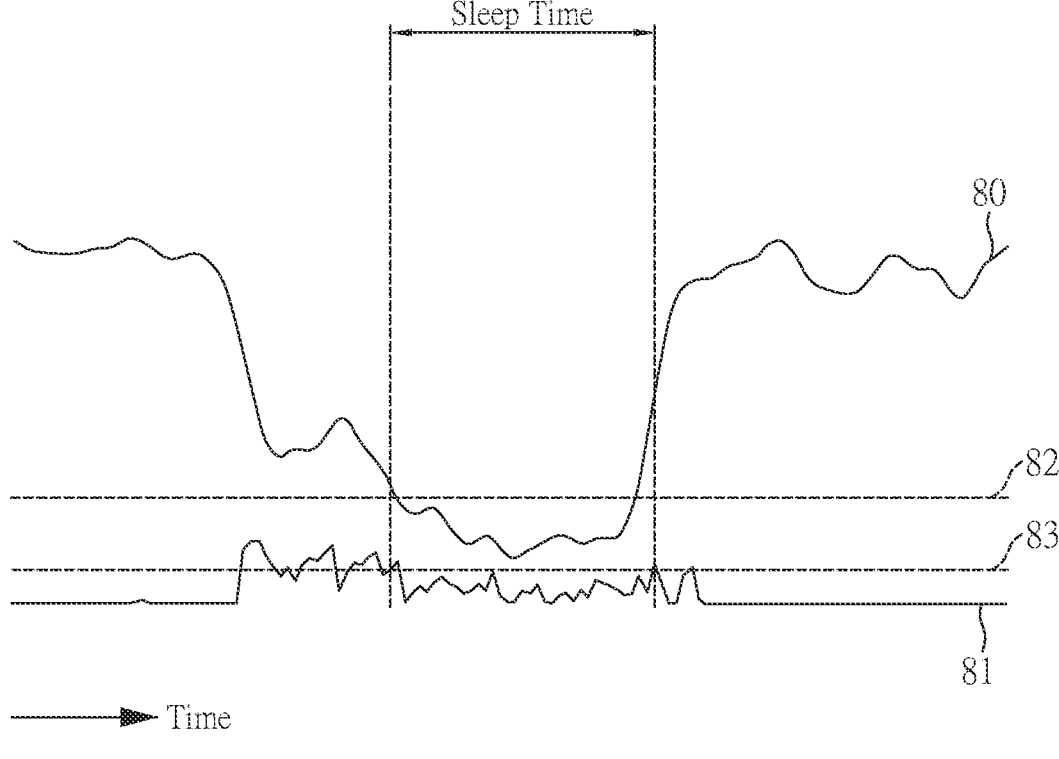
FIG. 8 is a schematic diagram showing a determination of a sleep time made after activity level standard deviation data and breathing variance data are obtained by the sleep monitoring method according to one embodiment of the present disclosure.

For example, reference can be made to FIG. 8, which is a schematic diagram showing a determination of a sleep time made after activity level standard deviation data and breathing variance data are obtained by the sleep monitoring method according to one embodiment of the present disclosure. As shown in FIG. 8, a data line 80 represents the breathing variance data, a data line 81 represents the activity level standard deviation data, a dotted line 82 represents a breathing variance threshold used to define a range of sleep breathing variance, and a dotted line 83 represents an activity level standard deviation threshold used to define a range of sleep activity level. As can be seen from FIG. 8, time intervals that are lower than both the breathing variance threshold and the activity level standard deviation threshold can be extracted through the dotted lines 82 and 83, and then the extracted time intervals can be determined as the sleep time. It should be noted that, for a continuous time segment, when the activity standard level deviation data meets a condition of being less than the activity level standard deviation threshold, and the breathing variance data simultaneously meets a condition of being smaller than the breathing variance threshold, a buffer time segment can be defined. The final sleep time can be determined by adding the buffer time segment before and after the continuous time segment. Since the statistical values obtained after recording the breathing rates and activity levels for a period of time in this embodiment are used as a criterion, the determined sleep time can be closer to a real sleep time of the user by considering the buffer time segment.

Step S35: performing a sleep quality estimation process to detect the sleep quality of the user during the sleep time based on the activity level data and the breathing data.

Reference is made to FIG. 9, which is a detailed flowchart of step S35 in FIG. 4. The processing circuit 16 can execute the sleep quality detection module D4 to execute the sleep quality estimation process in step S35, which can include the following steps:

Step S350: executing a noise reduction process on the activity level standard deviation data and the breathing variance data within the sleep time to obtain the smooth-processed activity level standard deviation data and the smooth-processed breathing variance data.

Step S351: classifying the time points within the sleep time into a plurality of sleep stages according to the activity level standard deviation data and the breathing variance data within the sleep time. The sleep stage can, for example, include a deep sleep stage and a light sleep stage, the deep sleep stage corresponds to a deep sleep activity level range and a deep sleep breathing variance range, and the light sleep stage corresponds to a light sleep activity level range and a light sleep breathing variance range. In this step, each of the time points can be classified into the deep sleep stage or the light sleep stage according to the activity level standard deviation data and the breathing variance data within the sleep time.

Figure 10:
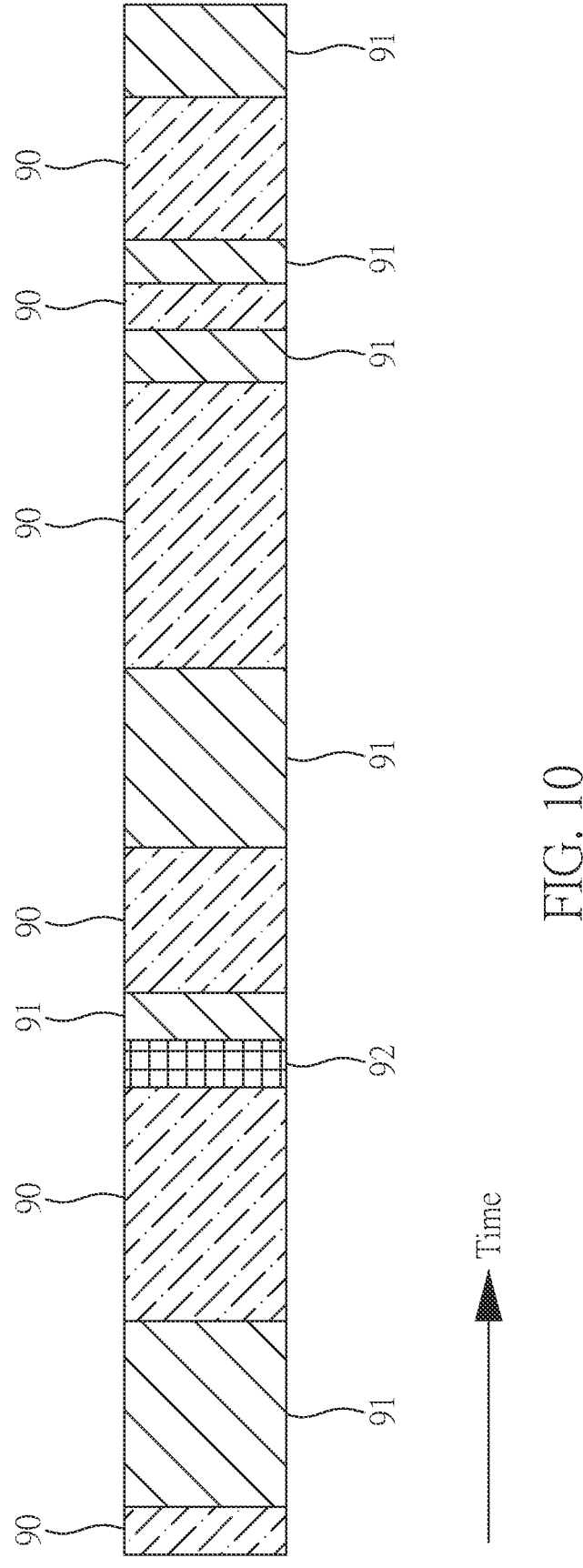
FIG. 10 is a schematic diagram of a determination result of a sleep stage according to one embodiment of the present disclosure.

Reference can be made to FIG. 10, which is a schematic diagram of a determination result of a sleep stage according to one embodiment of the present disclosure. As shown in FIG. 10, all the time points within the sleep time can be classified into sleep blocks 90, 91 and 92 as presented in FIG. 10. The sleep block 90 represents a light sleep stage block in which the activity level standard deviation data and the breathing variance data are within the light sleep activity level range and the light sleep breathing variance range, the sleep block 91 represents a deep sleep stage block in which the activity level standard deviation data and the breathing variance data are within the deep sleep activity level range and the deep sleep breathing variance range, and the sleep block 92 represents only the activity level standard deviation data that is not in the above activity level ranges defined by the deep sleep stage and the light sleep stage. The sleep block 92 can be specially marked as a block of high activity level stage, which is used to inform the user that there may be factors that cause high activity during sleep and need to be observed.

Step S352: determining the sleep quality of the user within the sleep time according to a distribution of the sleep stages within the sleep time.

Figure 11:
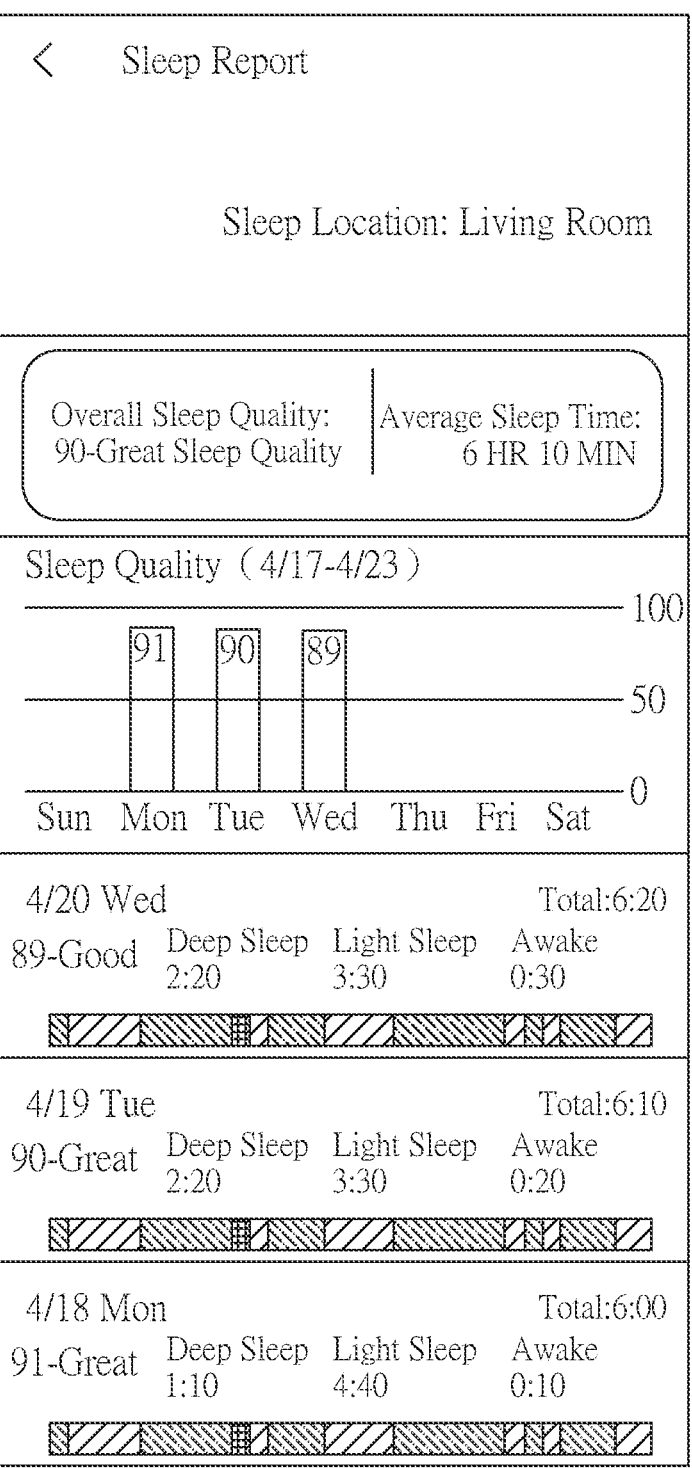
FIG. 11 is a schematic diagram of a sleep report generated by the sleep monitoring method according to one embodiment of the present disclosure.

For example, time corresponding to the deep sleep stage, light sleep stage, and high activity level stage obtained in the previous step can be counted, and different weights can be assigned to the above stages. Each segment of sleep time (or daily sleep time) can be rated according to percentages of the deep sleep stage, the light sleep stage, and the high activity level stage in the sleep time and the total sleep time. A score used for rating corresponds to the sleep quality, and a sleep report can finally be generated and provided to the user. Reference can be made to FIG. 11, which is a schematic diagram of a sleep report generated by the sleep monitoring method according to one embodiment of the present disclosure. For example, the sleep quality of each day can be displayed in a sleep report schematically shown in FIG. 10. Lengths of deep sleep time, light sleep time and wake-up time of each day can be counted, and daily and weekly comprehensive assessment for the sleep quality over a period of time can be made, while providing daily total sleep time and average sleep time over the period of time.

Reference is made to FIG. 3 again, where the sleep monitoring method proceeds to step S4: transmitting the generated sleep quality to the cloud server through the communication device.

For example, the processing circuit 16 can execute the communication processing module D5 to transmit the above-mentioned sleep quality and all related data to the cloud server 22 through the communication device 18, and the user device 24 can also directly communicate with the communication device 18 or the cloud server 22 to obtain the sleep report and display it in the user interface.

Beneficial Effects of the Embodiments

In conclusion, the sleep monitoring system and the sleep monitoring method provided by the present disclosure can realize the non-contact sleep monitoring technology based on wireless signals and completing an analysis of sleep quality in wireless terminal equipment, thereby allowing users to acquire more information about their sleep time and sleep quality.

In addition, in the sleep monitoring system and sleep monitoring method provided by the present disclosure, since statistical values are obtained after a period of time by recording the breathing rate and the activity level, and the statistical values of the breathing frequency and activity are assessed at the same time, such that the determination of the sleep state can be more accurate. Moreover, by setting the buffer time segment, the determined sleep time can also be closer to the real sleep time of the user.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A sleep monitoring system, comprising:
   a receiver disposed in a target field;
   a transmitter disposed within the target field, wherein the transmitter is configured to transmit a wireless detection signal to the target field, a user is located between the receiver and the transmitter, and the receiver is configured to receive the wireless detection signal through a plurality of communication links;
   a storage unit; and
   a processing circuit electrically connected to the receiver and the storage unit, wherein the processing circuit is configured to analyze a change of the wireless detection signal within a predetermined time, so as to detect a sleep time of the user within the predetermined time, and to calculate and obtain a sleep quality of the user during the sleep time;
   wherein the processing circuit is further configured to:
      obtain, from the wireless detection signal, channel state information (CSI) data of the communication links;
      execute a pre-processing process on the CSI data to calculate and obtain CSI amplitude data and CSI phase difference data of the CSI data;
      calculate and obtain activity level data of the user according to the CSI amplitude data;
      calculate and obtain breathing data of the user according to the CSI phase difference data;
      execute a sleep time detection process to detect the sleep time of the user within the predetermined time based on the activity level data and the breathing data; and
      perform a sleep quality estimation process to detect the sleep quality of the user during the sleep time based on the activity level data and the breathing data.

2. The sleep monitoring system according to claim 1, wherein the processing circuit is further configured to:
   store the obtained CSI data into a CSI buffer;
   determine whether or not a data volume of the CSI data in the CSI buffer is greater than a data volume set by a data window; and
   in response to the data volume of the CSI data in the CSI buffer being greater than the data volume set by the data window, execute the pre-processing process according to the CSI data in the CSI buffer.

3. The sleep monitoring system according to claim 1, wherein the pre-processing includes:
   calculating and obtaining a plurality of amplitudes and a plurality of phases of a plurality of subcarriers of the CSI data;
   selecting a subset associated with the user from the plurality of subcarriers;
   executing a principal component analysis (PCA) algorithm on the amplitudes and phase differences corresponding to the plurality of subcarriers in the subset to obtain principal components of the plurality of amplitudes and the plurality of phases; and
   executing a noise reduction algorithm on each of the principal components to generate the CSI amplitude data and the CSI phase difference data.

4. The sleep monitoring system according to claim 3, wherein the step of calculating and obtaining the breathing data of the user according to the CSI phase difference data includes:
   executing a Fourier transform algorithm on the CSI phase difference data to obtain a plurality of breathing rate data as the breathing data.

5. The sleep monitoring system according to claim 1, wherein the sleep time detection process includes:

determining whether or not data volumes of the activity level data and the breathing data exceed a predetermined data volume;

in response to the data volumes of the activity level data and the breathing data exceeding the predetermined data volume, calculating an activity level standard deviation data according to the activity level data, and calculating a breathing variance data according to the breathing data; and calculating and obtaining the sleep time of the user within the predetermined time period according to the activity level standard deviation data and the breathing variance data.

6. The sleep monitoring system according to claim 5, wherein the activity level standard deviation data and the breathing variance data respectively include a plurality of activity level standard deviations and a plurality of breathing variances corresponding to different multiple time points within the predetermined time, and the step of calculating the sleep time of the user within the predetermined time includes executing for each of the time points:

determining whether or not the activity level standard deviation and the breathing variance corresponding to a current time point are respectively within a sleep activity level range and a sleep breathing variance range: in the affirmative, determining that the current time point is a sleep time point, in the negative, determining that the current time point is a non-sleep time point.

7. The sleep monitoring system according to claim 6, wherein the sleep quality estimation process includes:

classifying the time points within the sleep time into a plurality of sleep stages according to the activity level standard deviation data and the breathing variance data within the sleep time; and determining the sleep quality of the user within the sleep time according to a distribution of the sleep stages within the sleep time.

8. The sleep monitoring system according to claim 7, wherein the sleep stages at least include a deep sleep stage and a light sleep stage, the deep sleep stage corresponds to a deep sleep activity level range and a deep sleep breathing variance range, the light sleep stage corresponds to a light sleep activity level range and a light sleep breathing variance range, wherein, in the sleep quality estimating process, each of the time points is classified into the deep sleep stage or the light sleep stage according to the activity level standard deviation data and the breathing variance data within the sleep time.

9. The sleep monitoring system according to claim 1, further comprising a communication device electrically connected to the processing circuit, wherein the communication device is configured to be connected to a cloud server through a network, and the obtained sleep quality is sent to the cloud server.

10. A sleep monitoring method, comprising:

disposing a receiver and a transmitter within a target area, wherein a user is located between the receiver and the transmitter;

configuring the transmitter to transmit a wireless detection signal to the target area, and configuring the receiver to receive the wireless detection signal over a plurality of communication links; and configuring a processing circuit electrically connected to the receiver and a storage unit to analyze a change of the wireless detection signal within a predetermined time, so as to detect a sleep time of the user within the predetermined time, and to calculate and obtain a sleep quality of the user during the sleep time, wherein the step of configuring the processing circuit to analyze the wireless detection signal to obtain the sleep time and the sleep quality further includes:

obtain, from the wireless detection signal, channel state information (CSI) data of the communication links;

execute a pre-processing process on the CSI data to calculate and obtain CSI amplitude data and CSI phase difference data of the CSI data;

calculate and obtain activity level data of the user according to the CSI amplitude data;

calculate and obtain breathing data of the user according to the CSI phase difference data;

execute a sleep time detection process to detect the sleep time of the user within the predetermined time based on the activity level data and the breathing data; and perform a sleep quality estimation process to detect the sleep quality of the user during the sleep time based on the activity level data and the breathing data.

11. The sleep monitoring method according to claim 10, further comprising configuring the processing circuit to:

store the obtained CSI data into a CSI buffer;

determine whether or not a data volume of the CSI data in the CSI buffer is greater than a data volume set by a data window; and in response to the data volume of the CSI data in the CSI buffer being greater than the data volume set by the data window, execute the pre-processing process according to the CSI data in the CSI buffer.

12. The sleep monitoring method according to claim 10, wherein the pre-processing process includes:

calculating and obtaining a plurality of amplitudes and a plurality of phases of a plurality of subcarriers of the CSI data;

selecting a subset associated with the user from the plurality of subcarriers;

executing a principal component analysis (PCA) algorithm on the amplitudes and phase differences corresponding to the plurality of subcarriers in the subset to obtain principal components of the plurality of amplitudes and the plurality of phase differences; and executing a noise reduction algorithm on each of the principal components to generate the CSI amplitude data and the CSI phase difference data.

13. The sleep monitoring method according to claim 12, wherein the step of calculating and obtaining the breathing data of the user according to the CSI phase difference data includes:

executing a Fourier transform algorithm on the CSI phase difference data to obtain a plurality of breathing rate data as the breathing data.

14. The sleep monitoring method according to claim 10, wherein the sleep time detection process includes:

determining whether or not data volumes of the activity level data and the breathing data exceed a predetermined data volume;

in response to the data volumes of the activity level data and the breathing data exceeding the predetermined data volume, calculating an activity level standard deviation data according to the activity level data, and calculating a breathing variance data according to the breathing data; and calculating and obtaining the sleep time of the user within the predetermined time period according to the activity level standard deviation data and the breathing variance data.

15. The sleep monitoring method according to claim 14, wherein the activity level standard deviation data and the breathing variance data respectively include a plurality of activity level standard deviations and a plurality of breathing variances corresponding to different multiple time points within the predetermined time, and the step of calculating the sleep time of the user within the predetermined time includes executing for each of the time points:

determining whether or not the activity level standard deviation and the breathing variance corresponding to a current time point are respectively within a sleep activity level range and a sleep breathing variance range; in the affirmative, determining that the current time point is a sleep time point, in the negative, determining that the current time point is a non-sleep time point.

16. The sleep monitoring method according to claim 15, wherein the sleep quality estimation process includes:

classifying the time points within the sleep time into a plurality of sleep stages according to the activity level standard deviation data and the breathing variance data within the sleep time; and determining the sleep quality of the user within the sleep time according to a distribution of the sleep stages within the sleep time.

17. The sleep monitoring method according to claim 16, wherein the sleep stages at least include a deep sleep stage and a light sleep stage, the deep sleep stage corresponds to a deep sleep activity level range and a deep sleep breathing variance range, the light sleep stage corresponds to a light sleep activity level range and a light sleep breathing variance range, wherein, in the sleep quality estimating process, each of the time points is classified into the deep sleep stage or the light sleep stage according to the activity level standard deviation data and the breathing variance data within the sleep time.

18. The sleep monitoring method according to claim 10, further comprising configuring a communication device electrically connected to the processing circuit to be connected to a cloud server through a network, and to send the obtained sleep quality to the cloud server.

* * * * *